US012376873B2

(12) United States Patent
Egan (10) Patent No.: US 12,376,873 B2
(45) Date of Patent: Aug. 5, 2025

(54) SURGICAL INSTRUMENT FOR BLUNT DISSECTION, DILATION OF INCISIONS, AND SEPARATION OF ADHESIONS

(71) Applicant: Egan Design LLC, Marblehead, MA (US)

(72) Inventor: Thomas D. Egan, Marblehead, MA (US)

(*) Notice: Subject to any disclaimer, the term of this patent is extended or adjusted under 35 U.S.C. 154(b) by 576 days.

(21) Appl. No.: 17/638,272

(22) PCT Filed: Aug. 27, 2020

(86) PCT No.: PCT/US2020/048151
§ 371 (c)(1),
(2) Date: Feb. 25, 2022

(87) PCT Pub. No.: WO2021/041636
PCT Pub. Date: Mar. 4, 2021

(65) Prior Publication Data
US 2022/0323093 A1    Oct. 13, 2022

Related U.S. Application Data

(60) Provisional application No. 62/892,353, filed on Aug. 27, 2019.

(51) Int. Cl.
*A61B 17/32*    (2006.01)
*A61B 90/00*    (2016.01)

(52) U.S. Cl.
CPC .............. *A61B 17/32* (2013.01); *A61B 90/02* (2016.02); *A61B 2017/320044* (2013.01); *A61B 2017/32006* (2013.01)

(58) Field of Classification Search
CPC .................... A61B 17/32; A61B 90/02; A61B 2017/320044; A61B 2017/32006
See application file for complete search history.

(56) References Cited

U.S. PATENT DOCUMENTS

| 4,249,536 | A | 2/1981 | Vega |
| 4,717,381 | A | 1/1988 | Papantonakos |
| 5,133,727 | A | 7/1992 | Bales et al. |
| 5,142,989 | A | 9/1992 | Suzumori et al. |
| 5,398,670 | A | 3/1995 | Ortiz et al. |

(Continued)

FOREIGN PATENT DOCUMENTS

| JP | 2005-253892 | 9/2005 |
| JP | 2009-106431 | 5/2009 |

*Primary Examiner* — Brooke Labranche
(74) *Attorney, Agent, or Firm* — Pandiscio & Pandiscio (57) ABSTRACT

Apparatus for blunt dissection, dilation of incisions, and separation of adhesions, the apparatus comprising: a frame; first and second belt supports mounted to the frame, the first and second belt supports being reconfigurable between a closed position and an open position; first and second continuous loop belts movably supported by the first and second belt supports, respectively, wherein the first and second continuous loop belts provide first and second outside surface face portions, respectively, and further wherein the first outside surface face portion is separated from the second outside surface face portion by a first distance when the first and second belt supports are in their closed position, and the first outside surface face portion is separated from the second outside surface face portion by a second, larger distance when the first and second belt supports are in their open position.

36 Claims, 8 Drawing Sheets

(56) References Cited

U.S. PATENT DOCUMENTS

| | | |
|---|---|---|
| 5,766,186 A | 6/1998 | Faraz et al. |
| 5,817,057 A | 10/1998 | Berenstein et al. |
| 5,878,783 A | 3/1999 | Smart |
| 5,919,128 A | 7/1999 | Fitch |
| 6,059,767 A | 5/2000 | Noriega |
| 6,332,865 B1 | 12/2001 | Borody et al. |
| 6,450,104 B1 | 9/2002 | Grant et al. |
| 6,517,477 B1 | 2/2003 | Wendlandt |
| 6,695,771 B2 | 2/2004 | Takada |
| 6,699,179 B2 | 3/2004 | Wendlandt |
| 6,702,734 B2 | 3/2004 | Kim et al. |
| 6,866,626 B2 | 3/2005 | Long et al. |
| 7,066,880 B2 | 6/2006 | Wendlandt |
| 7,087,011 B2 | 8/2006 | Cabiri et al. |
| 7,172,552 B2 | 2/2007 | Wendlandt |
| 9,326,663 B2 | 5/2016 | Viola |
| 2002/0107478 A1 | 8/2002 | Wendlandt |
| 2002/0173700 A1 | 11/2002 | Kim et al. |
| 2003/0050649 A1 | 3/2003 | Brock et al. |
| 2003/0093031 A1 | 5/2003 | Long et al. |
| 2005/0272976 A1 | 12/2005 | Tanaka et al. |
| 2006/0089533 A1 | 4/2006 | Ziegler et al. |
| 2007/0083081 A1 | 4/2007 | Schlagenhauf et al. |
| 2007/0167685 A1 | 7/2007 | Watanabe |
| 2008/0097292 A1 | 4/2008 | Cabiri et al. |
| 2008/0103440 A1 | 5/2008 | Ferren et al. |
| 2009/0024085 A1 | 1/2009 | To et al. |
| 2009/0028957 A1 | 1/2009 | Daniloff |
| 2009/0082722 A1 | 3/2009 | Munger et al. |
| 2009/0102281 A1 | 4/2009 | Diekevers et al. |
| 2011/0054257 A1 | 3/2011 | Stopek |
| 2013/0092719 A1 | 4/2013 | Kostrzewski |
| 2013/0150842 A1 | 6/2013 | Nau, Jr. et al. |
| 2016/0213231 A1 | 7/2016 | Viola et al. |

| Pulley 15 / Pulley 18 | Rotate CW | Stopped | Rotate CCW |
|---|---|---|---|
| Rotate CW | Yaw rotates CW, spread stays constant | Yaw rotates CW, spread increases | Yaw constant, spread increases |
| Stopped | Yaw rotates CW, spread decreases | Yaw constant, spread constant | Yaw rotates CCW, spread decreases |
| Rotate CCW | Yaw constant, spread decreases | Yaw rotates CCW, spread decreases | Yaw rotates CCW, spread stays constant |

Motions relative to view in Figure 2a

SURGICAL INSTRUMENT FOR BLUNT DISSECTION, DILATION OF INCISIONS, AND SEPARATION OF ADHESIONS

This patent application claims benefit of prior U.S. Provisional Patent Application Ser. No. 62/892,353, filed Aug. 27, 2019 by Egan Design LLC and Thomas D. Egan for SURGICAL INSTRUMENT FOR BLUNT DISSECTION, DILATION OF INCISIONS, AND SEPARATION OF ADHESIONS, which patent application is hereby incorporated herein by reference.

FIELD OF THE INVENTION

This invention relates to tools used to gently separate structures and to enlarge openings in a structure. More specifically, this invention relates to atraumatic blunt dissection of tissue in surgery, including but not limited to separation of tissues along tissue planes, enlarging openings in filmy visceral connective tissue (e.g., omentum), dilation of surgical openings in organs, and separation of adhesions in surgery. This invention will find particular utility in minimally invasive surgery (MIS) and in robotic-assisted surgery.

BACKGROUND OF THE INVENTION

In order to gain access to anatomy to be operated on in a surgical procedure, the surgeon will frequently need to carefully separate tissues along tissue planes or create and enlarge an opening in filmy, vascular tissue that connects and surrounds the abdominal organs, such as the greater and lesser omentum and its subdivisions. This process, known as blunt dissection, is generally time-consuming and tedious, and typically requires great skill and patience. Cutting these tissues with a scalpel or scissors ("sharp dissection") is usually contraindicated due to the risk of nicking one of the many blood vessels in the tissue. In open surgery a surgeon will often create a small opening and enlarge the opening with his or her fingers ("blunt dissection"), gently tearing the filmy material so as to create a larger opening without compromising the blood vessels.

In MIS and robotic-assisted surgery, small incisions prevent the direct use of hands and fingers in the blunt dissection process. The surgeon must therefore rely on instruments to accomplish this task. Typically, a grasping instrument with opposing jaws (e.g., forceps) is inserted in a small opening in the tissue (the small opening having been created by sharp dissection with a scalpel, scissors or an electrocautery device), and then the jaws are spread open so as to enlarge the opening. The angular orientation of the grasper jaws, and the slippery nature of the tissue on the (usually) metal instrument, make this a laborious task.

Another surgical task relevant to the present invention is the dilation of a small opening in an organ or tissue in order to permit the subsequent passage of an object larger than the initial opening. An example of this situation is in the use of a circular stapler to form an end-to-side or side-to-side anastomosis between an organ and another structure, such as joining the intestine to the stomach in gastric bypass surgery. In this example, a small opening is made in the stomach wall through which a circular stapler anvil must be passed. In order to staple the full circumference of the stomach opening, the opening in the stomach wall must be smaller than the circumference of the stapler anvil. It is therefore necessary to dilate or stretch-to-enlarge the small opening in order to permit passage of the stapler anvil through the opening in the stomach wall. Stomach tissue is somewhat elastic in nature so the stretched opening will close down somewhat after the stapler anvil has been passed through the dilated opening. The tools used to dilate the opening are generally the same forceps used in the blunt dissection described above and typically suffer the same difficulties.

Yet another surgical task that will benefit from the present invention is the separation of organs and tissue planes joined by adhesions. During surgery, the manipulations of organs and tissues can cause trauma to the tissue surface that result in the formation of scar tissue that cause the tissue and/or organs to stick together during healing. Sometimes these adhesions cause the patient discomfort and a second operation at a later date must be performed to separate these adhesions, or sometimes a patient with a chronic condition requires an operation in the same region as a previous operation and the surgeon must break up adhesions from the previous operation in order to gain access to the diseased anatomy. In cases where the adhesions are between two surfaces with a relatively large area, a tool must be used to gently separate tissue planes. This task again falls to the surgical forceps, with all the inherent difficulties and laboriousness cited above.

SUMMARY OF THE INVENTION

This invention seeks to overcome the present inadequacies in surgical blunt dissection, incision dilation and adhesion separation by the provision and use of a novel surgical instrument for gently expanding and separating tissues in a living body. It is an object of the present invention to provide a new surgical instrument with two or more expanding or separating surfaces that, preferably, remain approximately parallel during separation. It is further an object of the present invention to provide an instrument with striated or textured opposed surfaces to reduce slippage during tissue separation. It is still further an object of the present invention to provide an instrument where the striated or textured opposed surfaces move in a retrograde direction so as to assist in the advancement of the instrument through tissue. It is still a further object of the present invention to make the striated or textured opposed surfaces from a compliant or elastomeric material that is atraumatic to living tissue. It is yet another object of the present invention to provide the instrument in the form of an end effector at the distal end of an elongated shaft to facilitate use in minimally invasive surgery. It is still another object of the present invention to provide this end effector on an elongated shaft with means for articulation controllable by a surgeon through controls on a handpiece or through the control center of a surgical robotic system.

In one form of the invention, there is provided apparatus for blunt dissection, dilation of incisions, and separation of adhesions, the apparatus comprising:
a frame;
first and second belt supports mounted to the frame, the first and second belt supports being reconfigurable between a closed position and an open position;
first and second continuous loop belts movably supported by the first and second belt supports, respectively, wherein the first and second continuous loop belts provide first and second outside surface face portions, respectively, and further wherein the first outside surface face portion is separated from the second outside surface face portion by a first distance when the first and second belt supports are in their closed position, and the first outside surface face portion is separated from the second outside surface face portion by a second, larger distance when the first and second belt supports are in their open position.

In another form of the invention, there is provided a method for separating tissue, the method comprising:
providing apparatus comprising:
a frame;
first and second belt supports mounted to the frame, the first and second belt supports being reconfigurable between a closed position and an open position;
first and second continuous loop belts movably supported by the first and second belt supports, respectively, wherein the first and second continuous loop belts provide first and second outside surface face portions, respectively, and further wherein the first outside surface face portion is separated from the second outside surface face portion by a first distance when the first and second belt supports are in their closed position, and the first outside surface face portion is separated from the second outside surface face portion by a second, larger distance when the first and second belt supports are in their open position;
positioning the first and second belt supports in their closed position;
positioning the apparatus between two portions of tissue;
moving the first and second continuous loop belts on the first and second belt supports; and
positioning the first and second belt supports in their open position.

DETAILED DESCRIPTION OF THE PREFERRED EMBODIMENTS

Figure 1A:
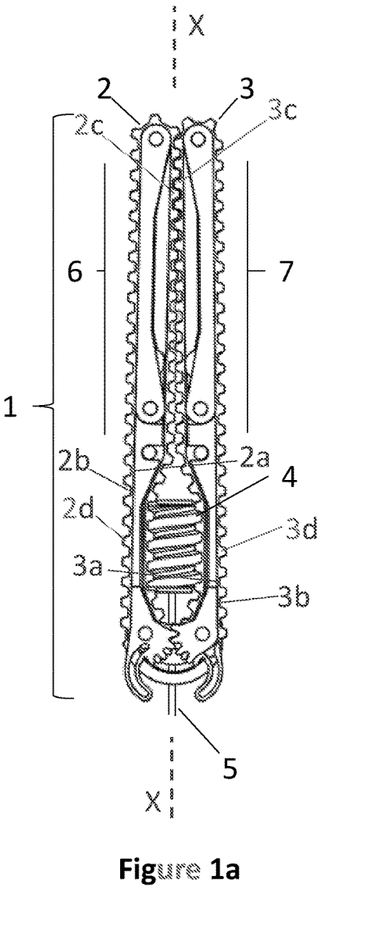
FIG. 1a shows a front view of a portion of the end effector of an embodiment of the present invention in the closed position, with the frame and pulley portions (see below) of the end effector removed for clarity of illustration.

FIG. 1a shows a portion of an end effector 1 of an embodiment of the present invention in a closed position. End effector 1 extends along a longitudinal axis X. In this embodiment, a first toothed belt 2 (comprising a continuous loop belt comprising an inside surface 2a and an outside surface 2b) and a second toothed belt 3 (comprising a continuous loop belt comprising an inside surface 3a and an outside surface 3b) engage a helical drive gear 4 driven by a rotatable drive shaft 5, e.g., protrusions 2c formed on inside surface 2a of first toothed belt 2, and protrusions 3c formed on inside surface 3a of second toothed belt 3, are engaged by the threads of helical drive gear 4, such that upon rotation of helical drive gear 4 by rotatable drive shaft 5, first toothed belt 2 and second toothed belt 3 will rotate. In embodiments where the end effector is articulating (described in detail below), shaft 5 is preferably a flexible torsion drive shaft.

In this embodiment, we can see that a first outside surface face portion 6 of first toothed belt 2 and a second outside surface face portion 7 of second toothed belt 3 are disposed approximately parallel to one another (and approximately parallel to longitudinal axis X). First toothed belt 2 and second toothed belt 3 have striated or textured surfaces ("belt teeth" 2d formed on outside surface 2b of first toothed belt 2 and "belt teeth" 3d formed on outside surface 3b of second toothed belt 3), are made of a compliant material (e.g., fiber-reinforced urethane or other belt material) and move in complementary continuous pathways in response to input from helical drive gear 4.

Figure 1B:
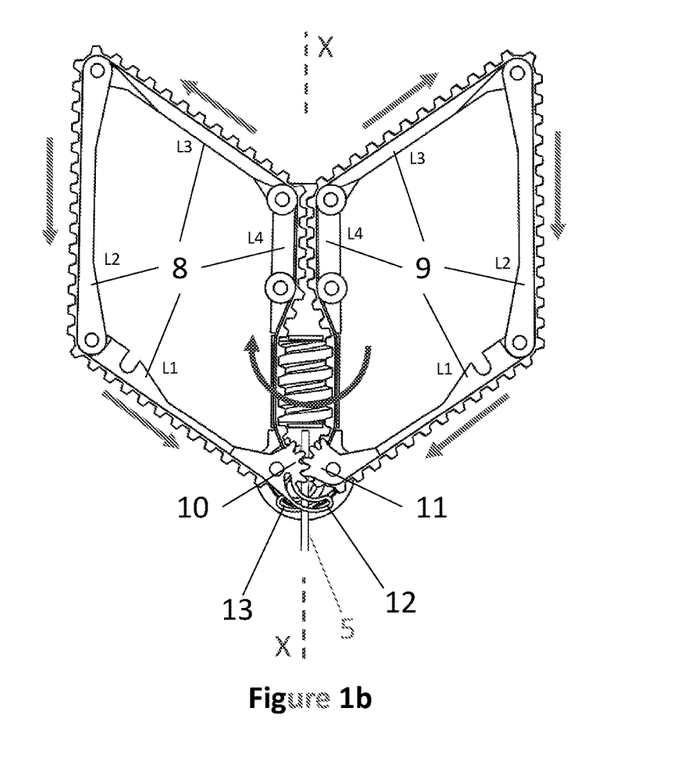
FIG. 1b shows a front view of a portion of the end effector of an embodiment of the present invention in the open position, with the frame and pulley portions (see below) of the end effector removed for clarity of illustration.

FIG. 1b shows the same portion of end effector 1 in an open position. In this view we can see first and second opposing four-bar linkages 8 and 9, respectively. Each of the first and second four-bar linkages comprises pivoting bar linkages L1-L4, and comprise rolling surfaces (not shown in FIG. 1b) concentric with the corner joints of the links over which the first and second toothed belts 2, 3 roll when driven by rotation of helical drive gear 4. As can be seen in FIG. 1b, the second link L2 of each four-bar linkage is pivotally mounted to the first link L1 of each four-bar linkage, the third link L3 of each four-bar linkage is pivotally mounted to the second link L2 of each four-bar linkage, and the fourth link L4 of each four-bar linkage is pivotally mounted to both the third link L3 of each four-bar linkage and the first link L1 of each four-bar linkage. In this embodiment the first and second opposing four-bar linkages 8, 9 are connected by first and second partial spur gears 10, 11 that assure equal and opposite reciprocal motion of the opposing four-bar linkages 8, 9 when driven by actuating means (see below) engaging first and second pin slots 12, 13 attached to first and second opposing four-bar linkages 8, 9, respectively. In this embodiment we can see that the spreading motion of first and second outside surface face portions 6, 7 of first and second opposing four-bar linkages 8, 9, respectively, approximately parallel to one another, and comprising striated or textured, compliant, and moving outside surfaces, would be useful in spreading and controlling tissues without slippage and with minimal trauma.

In other embodiments the first and second opposing four-bar linkages 8, 9, first and second toothed belts 2, 3, and/or helical drive gear 4 may be replaced by other means known to the art that impart the same or substantially equivalent properties to the first and second outside surface face portions 6, 7.

Figure 1C:
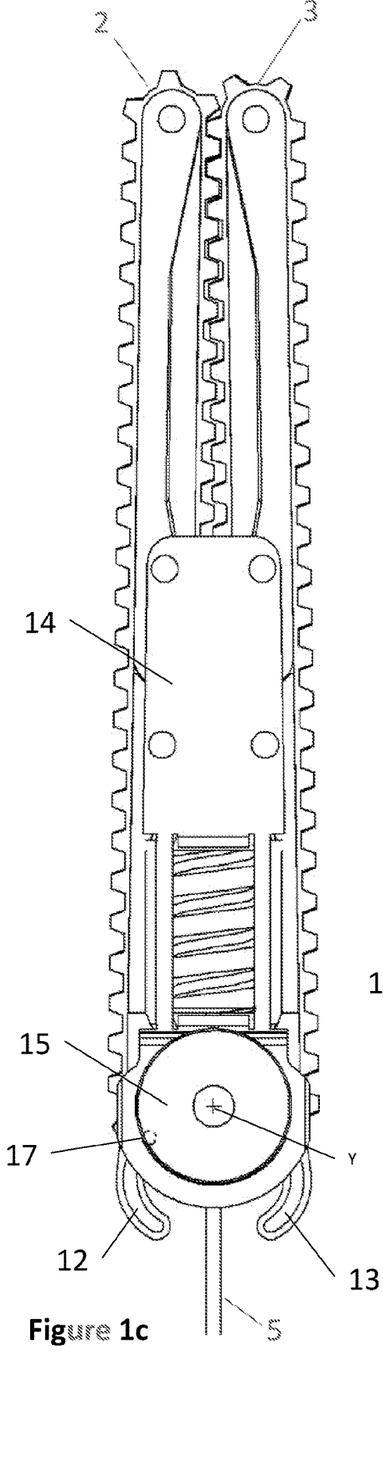
FIG. 1c shows the end effector of FIG. 1a with the frame and pulley portions included in the view.

FIG. 1c shows a frame 14 which ties the pivot points of link L4 of four-bar linkage 8, link L4 of four-bar linkage 9, and helical drive gear 4 to a common frame of reference. It will be appreciated that the first link L1 of each four-bar linkage is fixed to the frame 14, the second link L2 of each four-bar linkage is pivotally mounted to the first link L1 of each four-bar linkage, the third link L3 of each four-bar linkage is pivotally mounted to the second link L2 of each four-bar linkage, and the fourth link L4 of each four-bar linkage is pivotally mounted to both the third link L3 of each four-bar linkage and the first link L1 of each four-bar linkage. In an embodiment the actuating means for causing reciprocal motion of first and second opposing four-bar linkages 8, 9 comprises a pulley 15 having an eccentric pin 17 for engaging first pin slot 12 of link L1 of four-bar linkage 8. More particularly, pulley 15 is driven by a belt or cable (not shown) so as to rotate about an axis Y fixed within the reference of frame 14, with eccentric pin 17 (shown in phantom in FIG. 1c) engaged in first pin slot 12 which is part of link L1 of first four-bar linkage 8. In an embodiment where frame 14 is fixed in space (such as to the shaft of a larger surgical instrument), rotation of pulley 15 causes reciprocal motion of four-bar linkage 8 relative to frame 14 and, by virtue of the engagement of partial spur gears 10 and 11, also causes reciprocal motion of four-bar linkage 9 relative to frame 14.

Figure 1D:
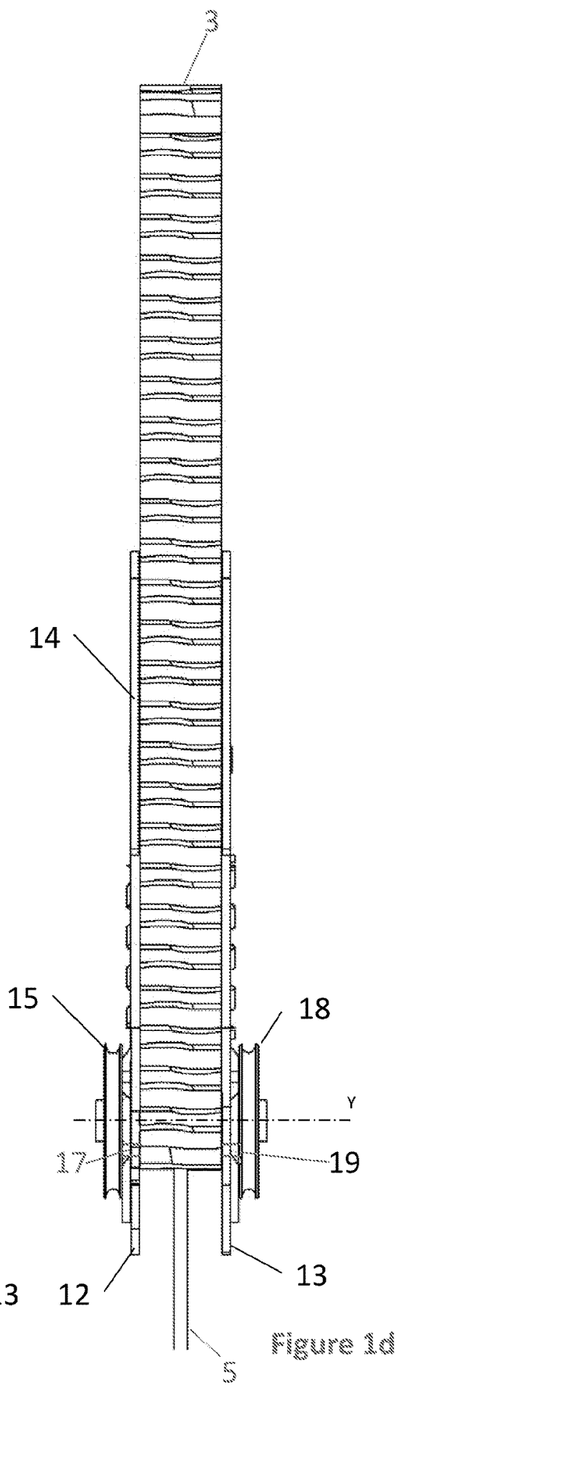
FIG. 1d is a side view of the end effector of FIG. 1c (with the frame and pulley portions included in the view).

In another embodiment a second pulley 18 (FIG. 1d) is provided. Second pulley 18 also rotates about axis Y and has an eccentric pin 19 engaging pin slot 13 which is part of link L1 of second four-bar linkage 9. In a version of this embodiment, frame 14 is fixed in space (such as to the shaft of a larger surgical instrument) and partial spur gears 10 and 11 are omitted. In this embodiment four-bar linkages 8 and 9 can move independently based on independent inputs from pulleys 15 and 18. In another (and preferred) version of this embodiment, partial spur gears 10 and 11 are provided and frame 14 is free to rotate about axis Y (which is fixed to a larger instrument, not shown in FIG. 1d).

Figure 2A:
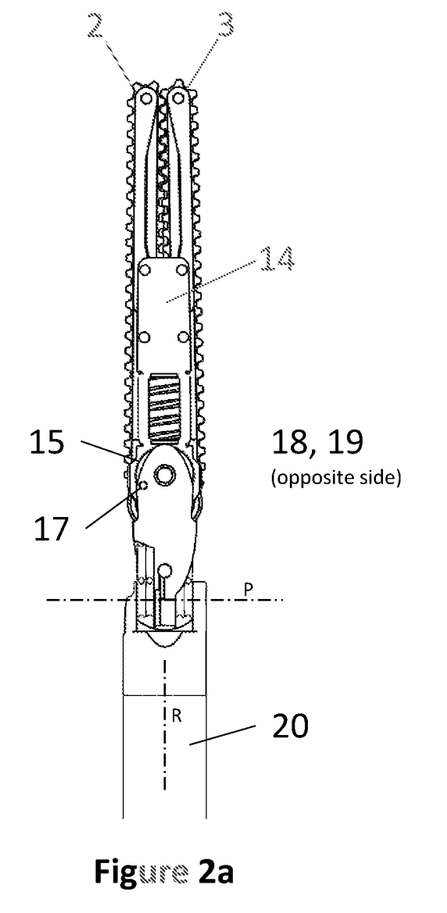
FIG. 2a shows a front view of the end effector of an embodiment of the present invention in the closed position, with the view further including means for articulation as might be employed in a robotic surgical instrument.
Figure 2B:
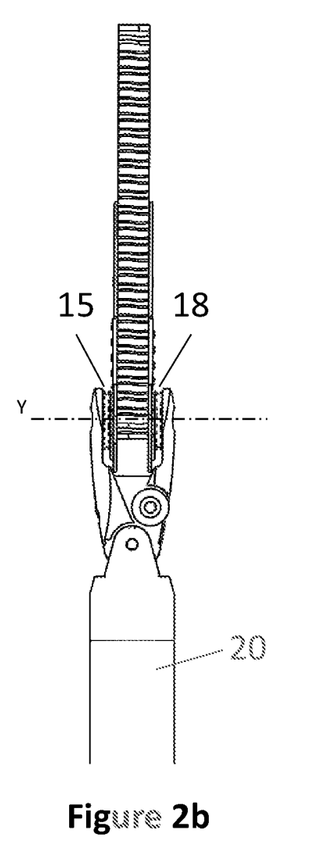
FIG. 2b shows a side view of the end effector of an embodiment of the present invention in the closed position, with the view further including means for articulation as might be employed in a robotic surgical instrument.

FIG. 2a shows a front view of the end effector 1 of an embodiment of the present invention as it might be disposed as part of an articulated instrument for robotic surgery with four degree of freedom movement, i.e., roll, pitch, yaw-1 and yaw-2. An elongated instrument shaft 20 rolls about axis R while the end effector pitches about axis P. FIG. 2b shows the side view of the same embodiment. The end effector moves in the yaw plane about axis Y. In an embodiment, roll, pitch and yaw movement are controlled by cables (not shown) interfacing with a surgical robot and which are in turn controlled by the inputs of a surgeon sitting at a robotic control center. The yaw axis includes first pulley 15 and second pulley 18 independently operated by the surgeon at the controller. First pulley 15 includes first eccentric pin 17 that engages first pin slot 12 connected to first four-bar linkage 8. Second pulley 18 includes off-center pin 19 (second pulley 18 and off-center pin 19 are on the opposite side of the view of FIG. 2a, and hence are not shown in FIG. 2a) that engages second pin slot 13 connected to second four-bar linkage 9. In this embodiment, first and second four-bar linkages 8, 9 are reciprocally connected by first and second partial spur gears 10, 11, assuring their motion is equal and opposite. In this way, when first and second pulleys 15, 18 rotate in the same direction (typically in response to finger movements by the surgeon at the robotic control station) the entire end effector rotates in the yaw plane. Contrary rotation of first and second pulleys 15, 18 will cause first and second outside surface face portions 6 and 7 to move apart or together.

Figure 2C:
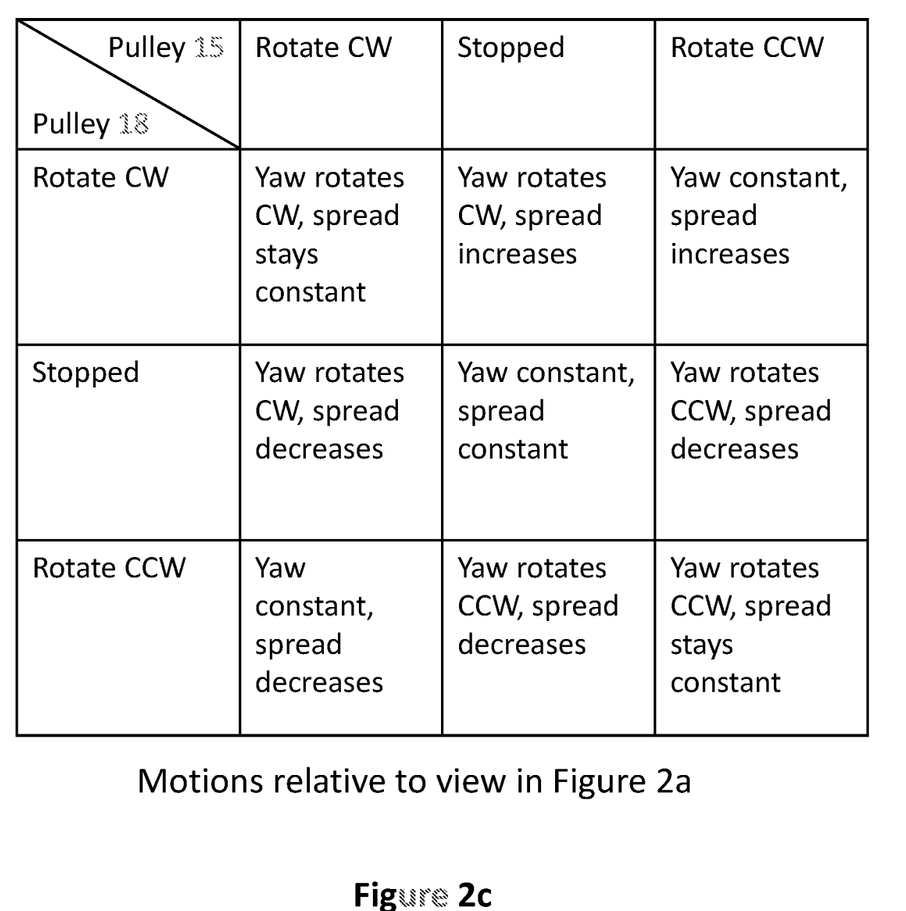
FIG. 2c is a matrix showing the relative motions of the end effector shown in FIGS. 2a and 2b, depending on the relative motions of the pulleys (see below) of the end effector.

FIG. 2c shows a table with the gross relationship of relative pulley movements from the vantage point of FIG. 2a. It should be understood that an infinite range of compound movements of the end effector, yawing, opening and closing, can be achieved by modulating rotational movements and speeds of the first and second pulleys 15, 18 as imparted by the surgeon's input.

Figure 3A:
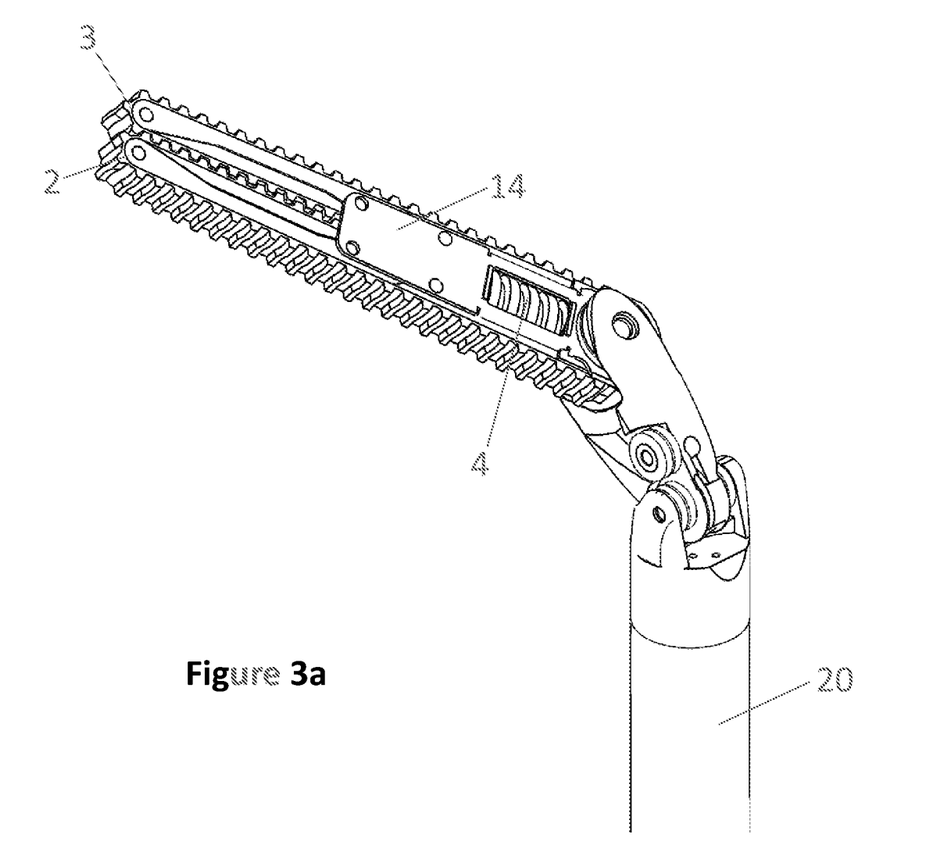
FIG. 3a shows an isometric view of the end effector of an embodiment of the present invention in the closed position, with the view further including means for articulation as might be employed in a robotic surgical instrument, and with the end effector being shown in an exemplary articulated position.

FIG. 3a shows an example of the end effector 1 moved in the pitch and yaw direction. In this embodiment, drive shaft 5 (not shown in FIG. 3a) is flexible and bends with articulations about the P and Y axes while still retaining the ability to drive helical gear 4.

Figure 3B:
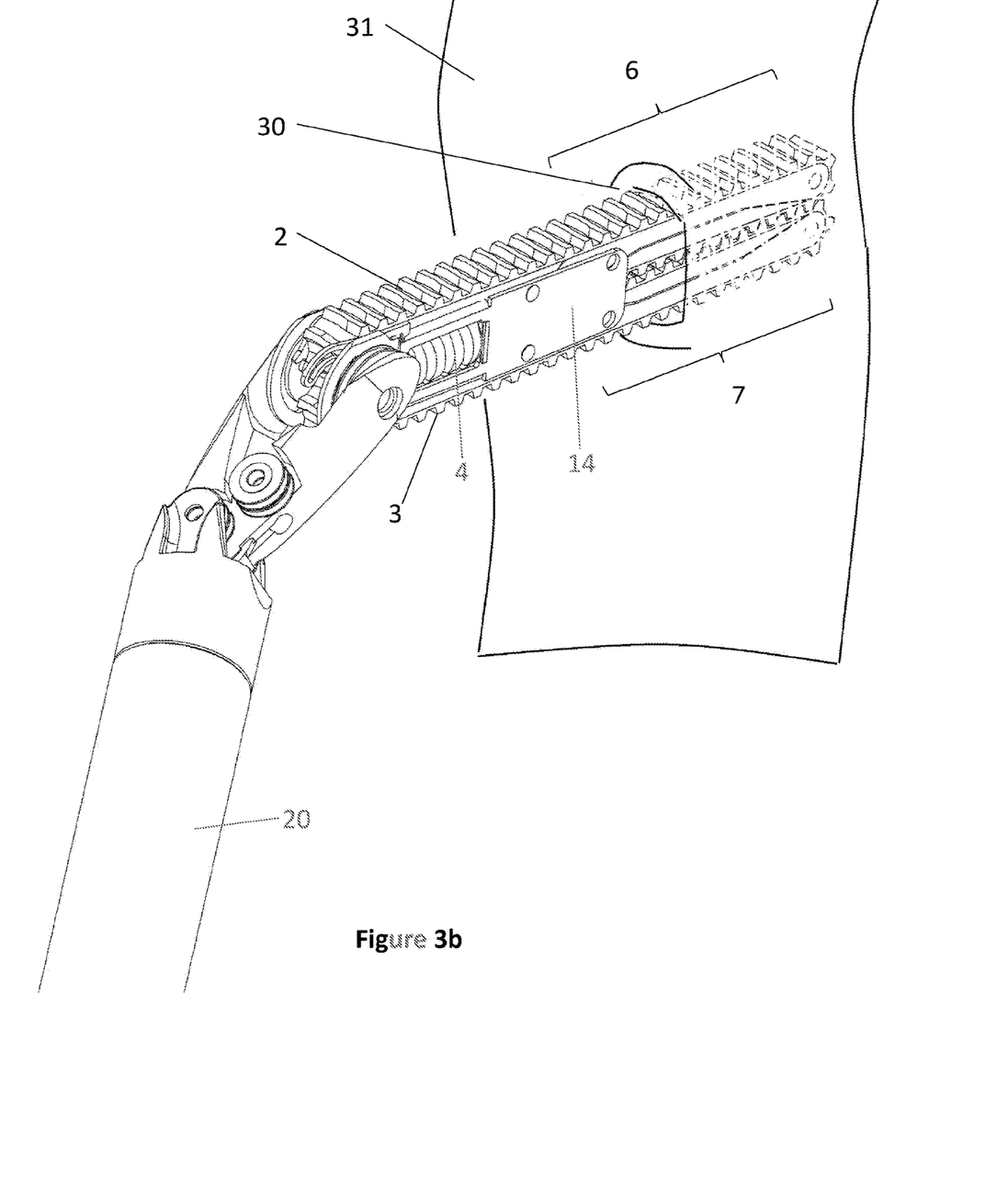
FIG. 3b shows the end effector of FIG. 3a being inserted into an opening in tissue while in its closed position.

FIG. 3b shows end effector 1 advanced into a small opening 30 in a portion of tissue 31 where a surgeon requires a larger opening for surgical access. Retrograde motion of the striated or textured surfaces (belt teeth 2d, 3d) on first and second outside surface face portions 6 and 7 of toothed belts 2 and 3 help to atraumatically guide the end effector into tight, small opening 30, separating tissue in the opening as the instrument advances.

Figure 3C:
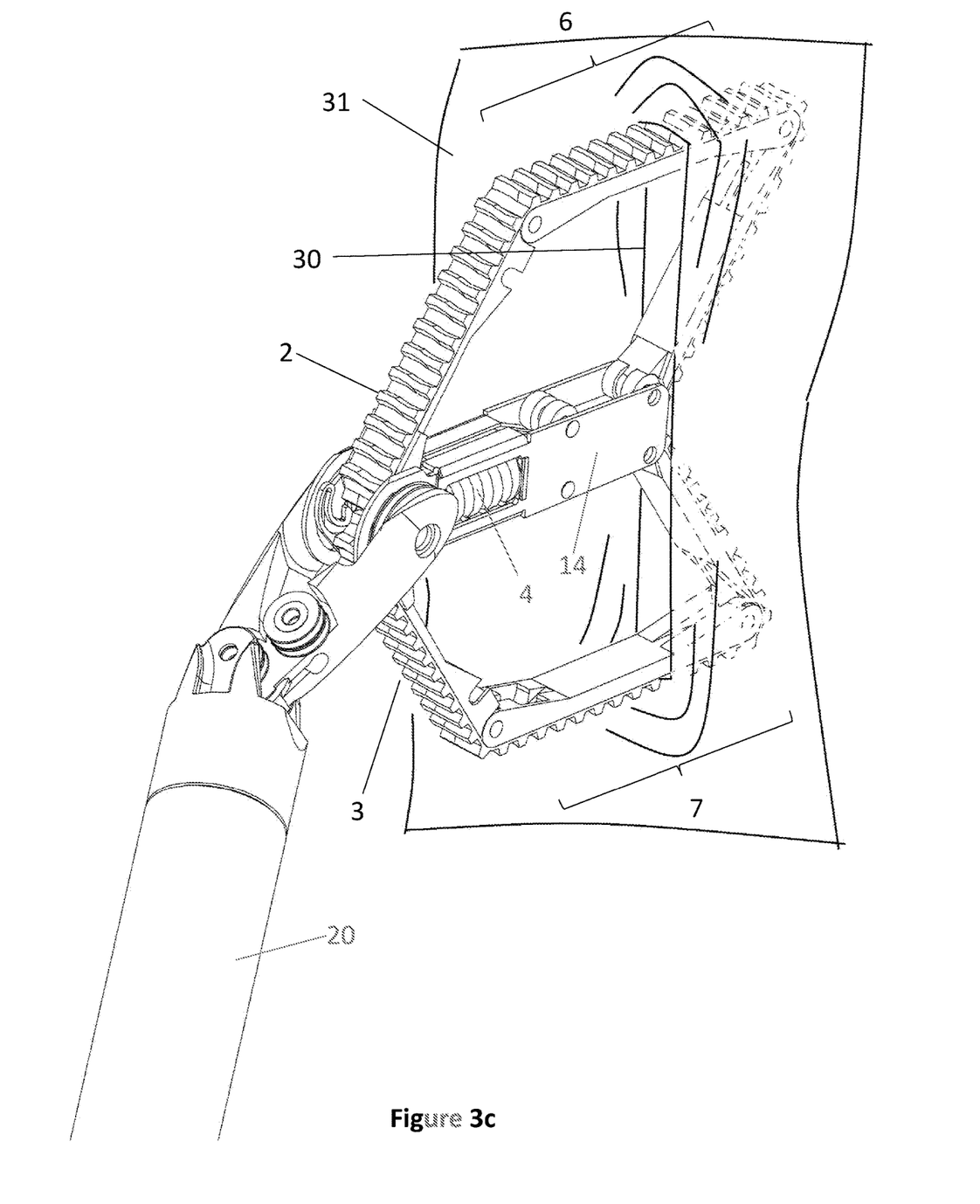
FIG. 3c shows the end effector of FIGS. 3a and 3b after the end effector has been reconfigured into its open position, whereby to dilate the opening in tissue.

FIG. 3c shows the opening 30 in tissue portion 31 further enlarged by the separation of first and second outside surface face portions 6 and 7. As first and second outside surface face portions 6 and 7 are approximately parallel and equipped with striated or textured surfaces (belt teeth 2d, 3d), the tissue is less likely to slide off the surfaces of the spreading instrument, giving the surgeon enhanced control of the tissue in blunt dissection, dilation of incisions and separation of adhesions.

Figure 4:
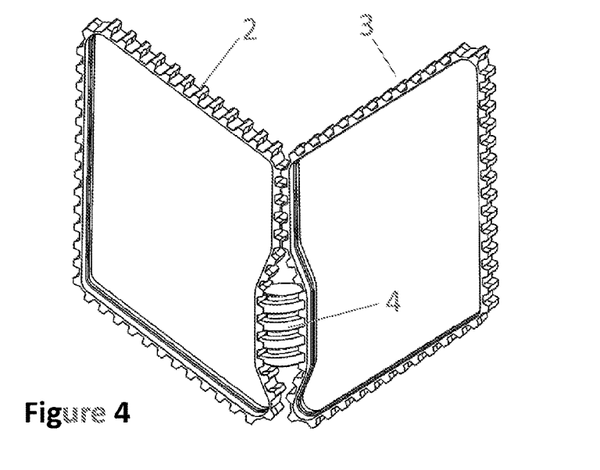
FIG. 4 shows a schematic view of an embodiment of the present invention, wherein the end effector presents a concave distal configuration.

FIG. 4 shows a schematic representation of the belt and helical gear arrangement in the embodiments described above wherein the distal end ("up" as shown on the page) opens in a concave "V" configuration. Note that in this construction, the two opposing belts 2, 3 are disposed in a single plane.

Figure 5:
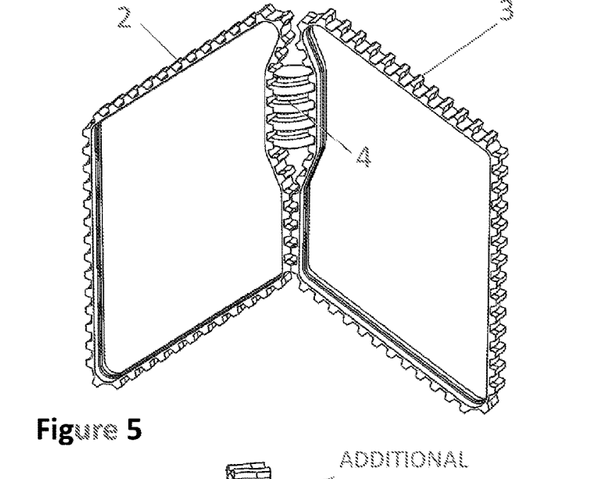
FIG. 5 shows a schematic view of an embodiment of the present invention, wherein the end effector provides a convex distal configuration.

FIG. 5 shows a schematic representation of another embodiment where the distal end of the instrument opens in a pointed wedge-shaped configuration (i.e., a convex "V" configuration). In this configuration the tip of the wedge shape could be introduced into an anatomical opening and the moving belt action would drive the wedge shape into the opening gently, forcing the opening to spread or dilate. Again, note that in this construction, the two opposing belts 2, 3 are disposed in a single plane.

Figure 6:
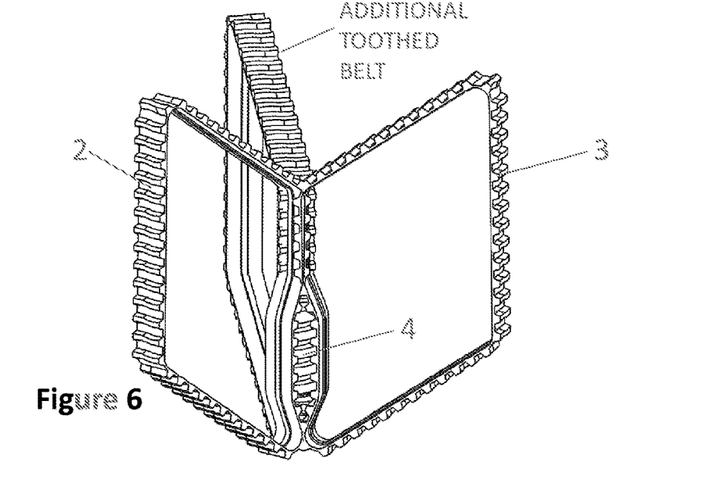
FIG. 6 shows a schematic view of an embodiment of the present invention, wherein the end effector comprises portions extending in multiple planes.

FIG. 6 shows still another embodiment where greater than two (in this case 3) outside surfaces spread in parallel for greater effect. In other words, with the construction of FIG. 6, three or more four-bar linkages, collectively providing three or more approximately parallel outer surfaces, are provided, whereby to provide greater effect. In one form of the invention, the three or more four-bar linkages are evenly distributed about the longitudinal axis of end effector 1 (i.e., where three four-bar linkages are provided, the three four-bar linkages are set 120 degrees apart, where four four-bar linkages are provided, the four four-bar linkages are set 90 degrees apart, etc.). In another form of the invention, the plurality of four-bar linkages are not evenly distributed about the longitudinal axis of end effector 1, e.g., the plurality of four-bar linkages do not have a symmetrical disposition about the longitudinal axis of the end effector. In the preceding description and accompanying figures, first pin slot 12 and second pin slot 13 are described as being arcuate. However, if desired, one or both of first pin slot 12 and second pin slot 13 could be formed as a straight, angled slot (i.e., a straight slot angled relative to the axis of link L1).

In the preceding description and accompanying figures, first outside surface face portion 6 and second outside surface face portion 7 are described as extending substantially parallel to one another (and parallel to the longitudinal axis X of end effector 1). However, it should be appreciated that, if desired, first outside surface face portion 6 and second outside surface face portion 7 may not extend substantially parallel to one another. By way of example but not limitation, first outside surface face portion 6 and second outside surface face portion 7 may incline toward one another (and toward the longitudinal axis X of end effector 1) as first outside surface face portion 6 and second outside surface face portion 7 extend in the distal direction. By way of further example but not limitation, one of first outside surface face portion 6 and second outside surface face portion 7 may incline toward the longitudinal axis X of end effector 1 and the other of the first outside surface face portion 6 and second outside surface face portion 7 may extend approximately parallel to the longitudinal axis X of end effector 1.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for blunt dissection, dilation of incisions, and separation of adhesions, the apparatus comprising:
   a frame;
   first and second belt supports mounted to the frame, the first and second belt supports being reconfigurable between a closed position and an open position; and
   first and second continuous loop belts movably supported by the first and second belt supports, respectively, wherein the first and second continuous loop belts provide first and second outside surface face portions, respectively, and further wherein the first outside surface face portion is separated from the second outside surface face portion by a first distance when the first and second belt supports are in their closed position, and the first outside surface face portion is separated from the second outside surface face portion by a second, larger distance when the first and second belt supports are in their open position;
   wherein the first and second belt supports each comprise four-bar linkages comprising a first link, a second link, a third link and a fourth link; and
   wherein the first link of each four-bar linkage is fixed to the frame, the second link of each four-bar linkage is pivotally mounted to the first link of each four-bar linkage, the third link of each four-bar linkage is pivotally mounted to the second link of each four-bar linkage, and the fourth link of each four-bar linkage is pivotally mounted to both the third link of each four-bar linkage and the first link of each four-bar linkage.

2. Apparatus according to claim 1 wherein the first and second outside surface face portions extend approximately parallel to one another.

3. Apparatus according to claim 1 wherein the first and second continuous loop belts comprise first and second inside surfaces, respectively, and further wherein the first and second inside surfaces ride on the first and second belt supports, respectively.

4. Apparatus according to claim 1 wherein the first and second continuous loop belts comprise first and second outside surfaces, respectively, and further wherein the first and second outside surfaces comprise belt teeth.

5. Apparatus according to claim 1 wherein the apparatus further comprises means for moving the first and second continuous loop belts on the first and second belt supports, respectively.

6. Apparatus according to claim 5 wherein the first and second continuous loop belts comprise first and second inside surfaces, wherein the first and second inside surfaces comprise projections, wherein the apparatus further comprises a helical drive gear rotatably mounted to the frame, and further wherein the helical drive gear engages the projections of the first and second inside surfaces such that rotation of the helical drive gear causes the first and second continuous loop belts to move on the first and second belt supports, respectively.

7. Apparatus according to claim 6 wherein the apparatus further comprises a rotatable drive shaft for rotating the helical drive gear.

8. Apparatus according to claim 1 wherein the apparatus further comprises means for moving the first and second belt supports between their closed and open positions.

9. Apparatus according to claim 1 wherein, when the first and second continuous loop belts are movably supported by the first and second belt supports, the first and second outside surface face portions of the first and second continuous loop belts are disposed adjacent to the third link of a four-bar linkage.

10. Apparatus according to claim 1 wherein the second link of at least one of the four-bar linkages comprises an arcuate pin slot, wherein the apparatus further comprises a pulley mounted to the frame, wherein an eccentric pin is mounted to the pulley, and wherein the eccentric pin is disposed in the arcuate pin slot, such that rotation of the pulley causes the eccentric pin to move in the arcuate pin slot and move that second link, whereby to cause the four-bar linkage of that second link to move between its closed and open positions.

11. Apparatus according to claim 10 wherein the four-bar linkages of the first and second belt supports are connected to one another by first and second partial spur gears, such that movement of one four-bar linkage between its closed and open positions causes similar movement of the other four-bar linkage between its closed and open positions.

12. Apparatus according to claim 1 wherein the second links of the four-bar linkages each comprise an arcuate pin slot, wherein the apparatus further comprises two pulleys mounted to the frame, wherein an eccentric pin is mounted to each of the pulleys, and wherein the eccentric pins are each disposed in one of the arcuate pin slots, such that rotations of the pulleys causes their eccentric pins to move in their associated arcuate pin slots and move their associated second links, whereby to cause the four-bar linkages of the associated second links to move between their closed and open positions.

13. Apparatus according to claim 12 wherein the four-bar linkages of the first and second belt supports are connected to one another by first and second partial spur gears.

14. Apparatus according to claim 1 wherein the first and second belt supports are co-planar.

15. Apparatus according to claim 1 wherein the first and second belt supports form a convex distal end when they are in their open position.

16. Apparatus according to claim 1 wherein the first and second belt supports form a concave distal end when they are in their open position.

17. Apparatus according to claim 1 wherein the apparatus further comprises a third belt support mounted to the frame, and a third continuous loop belt movably supported by the third belt support.

18. Apparatus according to claim 17 wherein the first, second and third belt supports are not co-planar.

19. A method for separating tissue, the method comprising: providing an apparatus comprising: a frame; first and second belt supports mounted to the frame, the first and second belt supports being reconfigurable between a closed position and an open position; first and second continuous loop belts movably supported by the first and second belt supports, respectively, wherein the first and second continuous loop belts provide first and second outside surface face portions, respectively, and further wherein the first outside surface face portion is separated from the second outside surface face portion by a first distance when the first and second belt supports are in their closed position, and the first outside surface face portion is separated from the second outside surface face portion by a second, larger distance when the first and second belt supports are in their open position; wherein the first and second belt supports each comprise four-bar linkages comprising a first link, a second link, a third link and a fourth link; and wherein the first link of each four-bar linkage is fixed to the frame, the second link of each four-bar linkage is pivotally mounted to the first link of each four-bar linkage, the third link of each four-bar linkage is pivotally mounted to the second link of each four-bar linkage, and the fourth link of each four-bar linkage is pivotally mounted to both the third link of each four-bar linkage and the first link of each four-bar linkage; positioning the first and second belt supports in their closed position; positioning the apparatus between two portions of tissue; moving the first and second continuous loop belts on the first and second belt supports; and positioning the first and second belt supports in their open position.

20. A method according to claim 19 wherein the first and second outside surface face portions extend approximately parallel to one another.

21. A method according to claim 19 wherein the first and second continuous loop belts comprise first and second inside surfaces, respectively, and further wherein the first and second inside surfaces ride on the first and second belt supports, respectively.

22. A method according to claim 19 wherein the first and second continuous loop belts comprise first and second outside surfaces, respectively, and further wherein the first and second outside surfaces comprise belt teeth.

23. A method according to claim 19 wherein the apparatus further comprises means for moving the first and second continuous loop belts on the first and second belt supports, respectively.

24. A method according to claim 23 wherein the first and second continuous loop belts comprise first and second inside surfaces, wherein the first and second inside surfaces comprise projections, wherein the apparatus further comprises a helical drive gear rotatably mounted to the frame, and further wherein the helical drive gear engages the projections of the first and second inside surfaces such that rotation of the helical drive gear causes the first and second continuous loop belts to move on the first and second belt supports, respectively.

25. A method according to claim 24 wherein the apparatus further comprises a rotatable drive shaft for rotating the helical drive gear.

26. A method according to claim 19 wherein the apparatus further comprises means for moving the first and second belt supports between their closed and open positions.

27. A method according to claim 19 wherein, when the first and second continuous loop belts are movably supported by the first and second belt supports, the first and second outside surface face portions of the first and second continuous loop belts are disposed adjacent to the third link of a four-bar linkage.

28. A method according to claim 19 wherein the second link of at least one of the four-bar linkages comprises an arcuate pin slot, wherein the apparatus further comprises a pulley mounted to the frame, wherein an eccentric pin is mounted to the pulley, and wherein the eccentric pin is disposed in the arcuate pin slot, such that rotation of the pulley causes the eccentric pin to move in the arcuate pin slot and move that second link, whereby to cause the four-bar linkage of that second link to move between its closed and open positions.

29. A method according to claim 28 wherein the four-bar linkages of the first and second belt supports are connected to one another by first and second partial spur gears, such that movement of one four-bar linkage between its closed and open positions causes similar movement of the other four-bar linkage between its closed and open positions.

30. A method according to claim 19 wherein the second links of the four-bar linkages each comprise an arcuate pin slot, wherein the apparatus further comprises two pulleys mounted to the frame, wherein an eccentric pin is mounted to each of the pulleys, and wherein the eccentric pins are each disposed in one of the arcuate pin slots, such that rotations of the pulleys causes their eccentric pins to move in their associated arcuate pin slots and move their associated second links, whereby to cause the four-bar linkages of the associated second links to move between their closed and open positions.

31. A method according to claim 30 wherein the four-bar linkages of the first and second belt supports are connected to one another by first and second partial spur gears.

32. A method according to claim 19 wherein the first and second belt supports are co-planar.

33. A method according to claim 19 wherein the first and second belt supports form a convex distal end when they are in their open position.

34. A method according to claim 19 wherein the first and second belt supports form a concave distal end when they are in their open position.

35. A method according to claim 19 wherein the apparatus further comprises a third belt support mounted to the frame, and a third continuous loop belt movably supported by the third belt support.

36. A method according to claim 35 wherein the first, second and third belt supports are not co-planar.

\* \* \* \* \*